(12) United States Patent
Zhang et al.

(10) Patent No.: US 9,884,036 B2
(45) Date of Patent: Feb. 6, 2018

(54) USES OF CHLOROGENIC ACID IN THE PREPARATION OF MEDICAMENTS FOR TREATMENT OF PSORIASIS

(71) Applicant: SICHUAN JIUZHANG BIOLOGICAL SCIENCE AND TECHNOLOGY CO., LTD, Chengdu, Sichuan (CN)

(72) Inventors: Jie Zhang, Sichuan (CN); Lina Zhu, Sichuan (CN)

(73) Assignee: SICHUAN JIUZHANG BIOLOGICAL SCIENCE AND TECHNOLOGY CO., LTD, Chengdu, Sichuan (CN)

( * ) Notice: Subject to any disclaimer, the term of this patent is extended or adjusted under 35 U.S.C. 154(b) by 0 days.

(21) Appl. No.: 15/513,401

(22) PCT Filed: Sep. 23, 2014

(86) PCT No.: PCT/CN2014/087211
§ 371 (c)(1),
(2) Date: Mar. 22, 2017

(87) PCT Pub. No.: WO2016/044999
PCT Pub. Date: Mar. 31, 2016

(65) Prior Publication Data
US 2017/0296500 A1  Oct. 19, 2017

(51) Int. Cl.
*A61K 31/235* (2006.01)
*A61K 31/216* (2006.01)
*A61K 9/00* (2006.01)

(52) U.S. Cl.
CPC .......... *A61K 31/216* (2013.01); *A61K 9/0014* (2013.01); *A61K 9/0053* (2013.01)

(58) Field of Classification Search
CPC ...................................................... A61K 31/22
USPC .......................................................... 514/533
See application file for complete search history.

(56) References Cited

U.S. PATENT DOCUMENTS

2011/0165096 A1* 7/2011 Liu ........................ A61K 36/60
424/45

FOREIGN PATENT DOCUMENTS

JP          2007223948 A    9/2007
KR    10-2014-0093435 A    7/2014
WO         2014065194 A1    5/2014

* cited by examiner

*Primary Examiner* — Raymond J Henley, III
(74) *Attorney, Agent, or Firm* — Novick, Kim & Lee, PLLC; Allen Xue

(57) ABSTRACT

The present invention provides uses of chlorogenic acid in the preparation of medicaments for treatment of psoriasis. Chlorogenic acid, a small molecular compound, is a biological response modifier focusing on the overall regulation, and has a good effect on rebuilding the homeostasis of immune function. Harmful action of chlorogenic acid on liver and kidney is not found, and it can be long-term used, without toxic and side effects on body. Chlorogenic acid is safe and effective, with low recurrence rate, and it can improve life quality of patients. It has an obvious effect on psoriasis, especially on psoriasisvulgaris and psoriasis pustulosa, thus for treatment of psoriasis, chlorogenic acid has a wide application prospects.

6 Claims, 2 Drawing Sheets

USES OF CHLOROGENIC ACID IN THE PREPARATION OF MEDICAMENTS FOR TREATMENT OF PSORIASIS

TECHNICAL FIELD

The present invention relates to uses of chlorogenic acid in the preparation of medicaments for treatment of psoriasis.

BACKGROUND ART

Psoriasis, commonly called "oxhide lichen", is a common and recurrent skin disease with chronic inflammation, and characterized by mica-like scale, red membrane sign, punctuate hemorrhage, with an incidence rate of about 0.123% in China. In recent years, the incidence of psoriasis shows tendency to ascend, and in the initial stage, psoriasis has an apparent seasonality, and presents severity in winter and light in summer. At present, the cause of disease is unknown, and effective therapeutic method is deficient.

Currently, psoriasis includes four types, i.e. psoriasisvulgaris, psoriasis arthropathica, erythroderma psoriaticum, and psoriasis pustulosa, in which psoriasisvulgarisaccounts for above 99% of psoriasis. Psoriasisvulgaris is an ordinary psoriasis, while the other three types are called specific psoriasis. According to experience summarization of famous doctors of traditional Chinese medicine in successive dynasties, psoriasisvulgaris is generally classified as four types, i.e. blood-heat type (blood-heat and wind-dryness type), blood-deficiency type (blood-deficiency and wind-dryness type), blood-dryness type, blood stasis type (thedermalhematomalikelytype); for special psoriasis, pustule type is generally discriminated as sepsis type (damp-heat and accumulated toxin type), and erythroderma type is poison and heat type (blood-heat toxic pattern), and joint type is cold-dampness or rheumatic arthralgia type.

Primary clinical manifestations of psoriasis vulgaris include white scale, shining thin film and punctuate hemorrhage. Main pathologic manifestations include: parakeratosis, visible microabscess (Munro's abscess) arising from neutrophilic granulocyte, granular layer thinning or vanishing; acanthosis, trochanterellus extension; blood vessels in dermal papilla distort and expand, and vessel wall slightly thickens; superior part of dermis is infiltrated by inflammatory cells of from mild to moderate. Psoriasis vulgaris is more common, and approximately occupied above 90%.

Psoriasis pustulosa is a type of psoriasis having more severe pathogenetic condition and divided into generalized psoriasis and localized psoriasis. In clinical, it is characterized by generalized erythema spreading whole body, as well as sterile pustules with a miliary size, and frequently accompanied by hyperpyrexia and increase of white blood cell and hypoproteinemia, even can threaten to life. This type is rarer in clinic, and accounts for about 0.77% of patients with psoriasis.

Tissue pathology of psoriasis is that epidermic keratinocytes cannot fully matured, and spaces between cell bundles fill with air and refract ray to form silver mica-like scale, as seen in clinical; intradermal papilledema swells and intrudes into epidermis, getting close to corneum layer, and in clinical, scraping scales may impair papilla blood vessels and produce punctuate hemorrhage. Medical doctors consider that development of psoriasis is mainly related to functional disorder of autoimmunity, metabolism and endocrine, but climatic change, labile mood, infection, trauma and so on are causative factors.

Pathogenesis of psoriasis is complex, and at present, it is not completely interpreted. The pathogenesis may roughly be summarized as follows: on the basis of certain genetic backgrounds, various causative agents stimulate the immune system of organisms, and cause functional disorders of immune system focusing on T cells. Inflammatory cells migrate to epidermis and locally infiltrate, resulting in part inflammation and paraplasm of keratinocytes, and finally resulting in occurrence of pathologic change of psoriasis.

Psoriasis is a common chronic inflammatory skin disease, with hyperplasia of keratinocytes, infiltration of inflammatory cells, and neovascularization as main pathologic changes, and is a commonly encountered disease and a frequently occurring disease in department of dermatology. Etiology of this disease is unknown, and its treatment is difficult, and it cannot be completely eradicated. Currently, western medicaments tretinoin and immunosuppressive agents are used to treat this disease, especially possessing advantages in controlling psoriasis activity, but they have problems including more adverse reactions and high recurrence rate following drug withdrawal, etc.

CONTENTS OF THE INVENTION

The technical solution of the present invention provides new uses of chlorogenic acid.

Uses of chlorogenic acid of the present invention in the preparation of medicaments for treatment of psoriasis.

Wherein, said medicaments are prepared using an effective amount of chlorogenic acid as active ingredient and pharmaceutically acceptable adjuvants or auxiliary ingredients. Said medicaments are those treating psoriasisvulgaris and psoriasis pustulosa.

Wherein, said pharmaceutical preparation contains 1-3000 mg chlorogenic acid per preparation unit.

Wherein, the dosage of chlorogenic acid used in said pharmaceutical preparation is 10-40 mg/kg.

Wherein, said medicament is oral preparations, external preparations or injections.

Psoriasis is a chronic inflammatory and proliferative skin disease with immunologic abnormality, that is determined by polygenic inheritance and induced by many environmental factors. Worldwide, the prevalence in natural population is 0.1%-3%, while the prevalence in China is 0.123%, and the annual incidence is 0.1%. Although this disease does not endanger people's lives, the course of disease is long, and it is stubbornlyintractable. Serious person may develop a disabling psoriatic arthritis, erythroderma psoriaticum, and even involve eyes, liver, kidney, cardiovascular, lung and similar organs, thus severely affect life quality of patients. Some patients can have psychological disorders such as blushing, stress, anxiety, depress, etc., and are not willing to take part in social activities, affect their daily living, create deep suffering for patients' body and psychology. Because of recurrent attacks of this disease, repeat treatment is needed, and thus bring a heavy economic burden to patients and their family. Currently, psoriasis cannot be completely eradicated. Except for traditional Chinese medicines, traditional treatment mostly focuses on immunosuppressive agents and retinoids, and long-term administration of these medicaments may easily produce seriously adverse effects including dependence and damage on liver and kidney.

Chlorogenic acid, a small molecular compound, is a biological response modifier focusing on the overall regulation, and has a good effect on rebuilding the homeostasis of immune function. Harmful action of chlorogenic acid on liver and kidney is not found, and it can be long-term used, without toxic and side effects on body. Chlorogenic acid is safe and effective, with low recurrence rate, and it can improve life quality of patients. It has an obvious effect on psoriasis, especially on psoriasisvulgaris and psoriasis pustulosa, thus for treatment of psoriasis, chlorogenic acid has a wide application prospects.

EXAMPLES

Example 1 Pharmacodynamic Test of Chlorogenic Acid According to the Present Invention for Treatment of Psoriasis (Psoriasis Vulgaris Model)

Experimental study:
1. Materials
1) Animals
Male guinea pigs, weighing 350-400 g, are provided by the Experimental Animal Center of Sichuan University. Animal grade: first class; license number: No. 10.
2) Drugs and Reagents
Acitretin A capsule is purchased from Chongqing Hua-Pont Pharm. Co., Ltd, with a batch number: 2013010.
Chlorogenic acid is provided by Sichuan Jiuzhang Biochemical Science and Technology Development, Co. Ltd, with a batch number: 130601.
100 g of 5% propranolol dinitrate raw materials is purchased from Hubei Kangbaotai Fine Chemicals Co. Ltd., with a batch number 20130525.
Emulsion bases are provided by Department of Pharmaceutics, West China School of Pharmacy, Sichuan University.
2. Experimental Methods
1) Establishing Model and Grouping
60 guinea pigs adapted to diet one week before initiation of experimentation, and both ears of guinea pigs were unhaired, and randomly divided into blank group and experimental group, with 12 guinea pigs for blank group and 48 guinea pigs for experimental group. In experimental group, 5% propranolol dinitrate emulsion was evenly applied to bilateral ear back of guinea pigs, while in blank group, blank medium was applied for 14 days, with a thickness of about 1.0 mm for each time and 4 times per day, to induce pathologic change of psoriasis vulgaris-appearing. After 14 days, two animals of blank group and four animals of experimental group were used for pathologic detection, and results showed ear tissues of guinea pigs presented parakeratosis and hyperkeratosis, thinning of stratum granulosum, infiltration of phlogocytes, vasodilatation of superficial dermis, mastoid extrusion, indicating success of model establishment. Based on body weight and conditions of establishing model, the remaining 44 guinea pigs were divided into 4 groups using random digits table, i.e. model group, positive group, low-dose group of chlorogenic acid, high-dose group of chlorogenic acid, 11 guinea pigs for each group.

Figure 1:
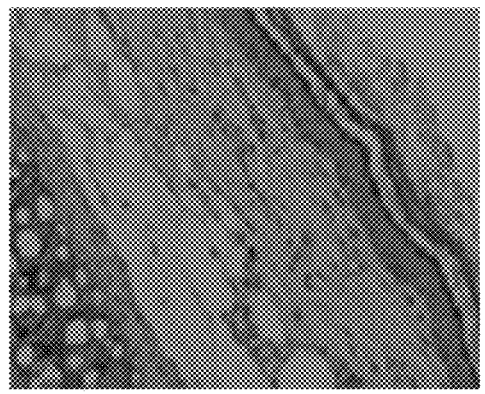
FIG. 1 Blank group
FIG. 2 Model group
FIG. 3 Positive group
FIG. 4 Low-dose group of chlorogenic acid
FIG. 5 High-dose group of chlorogenic acid
FIG. 6 Baker scores for psoriasiform pathological change in aural region of guinea pigs of each group (Note: comparing with the blank group, **$P<0.01$; comparing with the model group, ##$P<0.01$).
Figure 2:
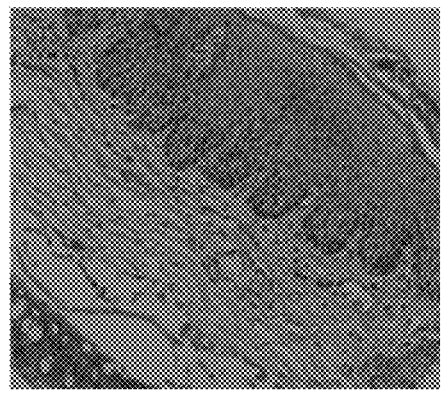
Figure 3:
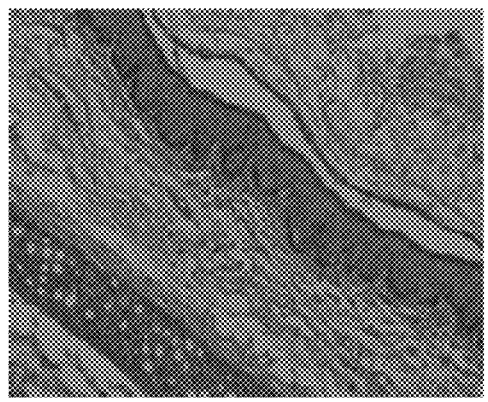
Figure 4:
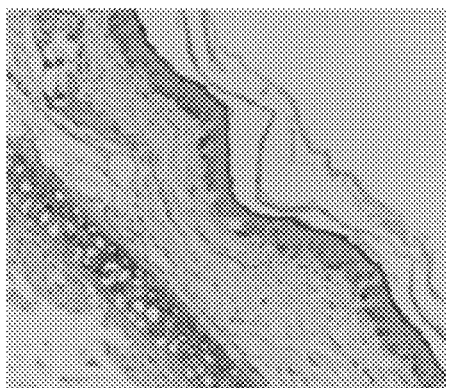
Figure 5:
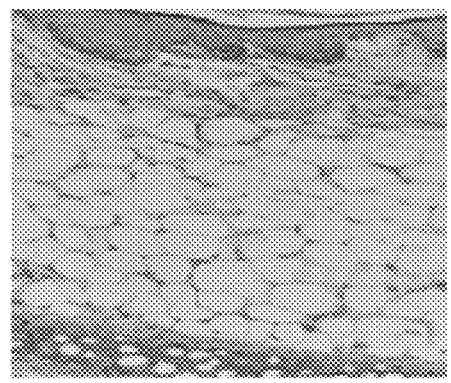
Figure 6:
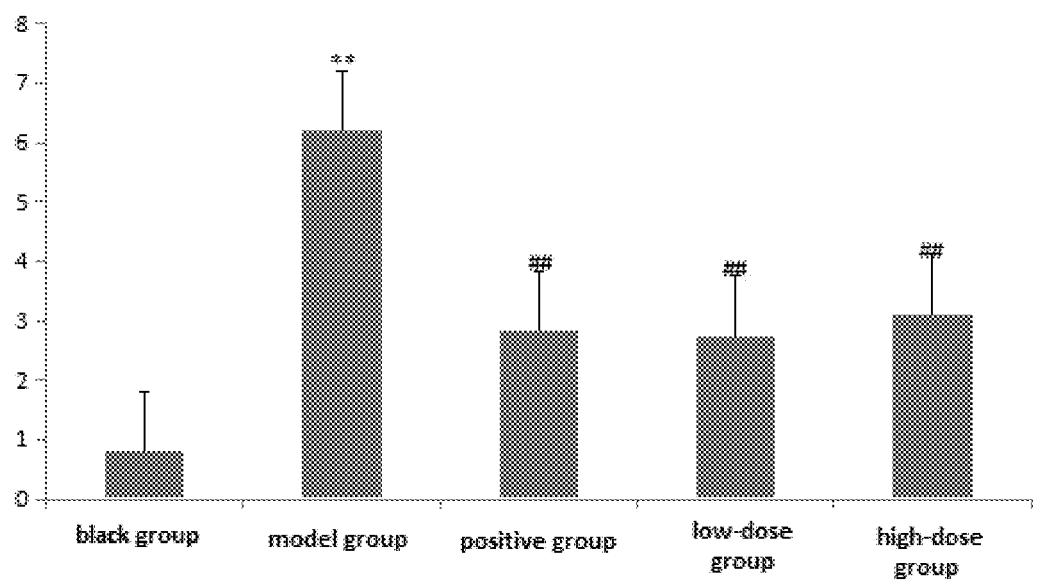

2) Administration
0.9% sodium chloride solution was administrated to blank group and model group; Positive drug control group was given suspension of acitretin A capsule at 2.25 mg/kg, and the amount of intragastric administration is all 1 mL/100 g for each time, twice a day; 20 mg/kg chlorogenic acid was administrated to the low-dose group by intramuscular injection, and 40 mg/kg chlorogenic acid was administrated to the high-dose group by intramuscular injection, using a volume of 0.2 ml/10 g, once a day.
3) Sampling and Processing
After administrating for 14 days, samples were taken, and 12% chloral hydrate was peritoneally injected at a dose of 0.35 mL/100 g. After anesthesia, blood sample was collected from abdominal aorta, and animals were sacrificed. Both ear tissues of guinea pigs were scissored and fixed in 10% formaldehyde solution. Ear tissues of guinea pigs were taken out, embedded in paraffin, sliced, normally stained with HE, and sealed with neutral gum. Pathological change of ears was observed under optical microscope, investigated and taken a picture in 10×20 vision. Referring to Baker method, pathologic scores of tissues were assessed: the presence of Munro microabscess in corneum layer scores 2.0 point; hyperkeratosis scores 0.5 point; parakeratosis scores 1.0 point; stratum granulosum thinning and disappearing scores 1.0 point; acanthosis scores 1.0 point; skin process extension and tortuous basal lamina are marked 0.5, 1.0, 1.5 according to light, middle, and heavy degrees, respectively; mononuclear cells and polymorphonuclear cells infiltration in dermis is marked 0.5, 1.0, 1.5 according to light, middle, and heavy degrees, respectively; obvious mastoid extrusion scores 0.5 point; telangiectasis in superficial layer of dermis scores 0.5 point.
4) Effects on Hepatic and Renal Function
Before guinea pigs were sacrificed, blood was drawn via peritoneal cavity, and urea nitrogen and creatinine were detected by enzymic method, while glutamate pyruvate transaminase and glutamic-oxalacetic transaminase were tested using rate method.
3. Statistical Analysis
All values were processed using SPSS13.0 software, and the experimental results were presented as $\bar{x}\pm s$. $p<0.05$ was considered to be a statistical difference. The mean of multi-samples were compared using analysis of variance.
4. Results
1) Results observed by light microscope showed that corneum layer of blank group was thin and presented cancellated interlace, and almost no stratum granulosum was clear, with 1-2 layers; 3-5 layers of stratum spinosum cells; the basal lamina was monolayer cylindric cells, and cuticular process was flat; capillarectasia was not found in superficial layer of dermis, but a small amount of lymphocytes were distributed. Model group presented hyperkeratosis and parakeratosis, thinning or disappearing of stratum granulosum, acanthosis, telangiectasis in dermis and similar phenomenons, as well as mild and moderate infiltration of phlogocytes can also be seen in dermis layer. After administration, for positive group and chlorogenic group, pathology of lesional tissue showed obvious improvement. Pathological sections for aural region of guinea pigs were shown in FIGS. 1-5, and Baker scores for pathologic change of psoriasis in aural region of guinea pigs of each group were shown in FIG. 6.
Statistical results showed that compared with model group, Baker scores of blank group and each drug group were significantly different ($P<0.01$), indicating models were successfully made, and that each drug administration group was effective in ameliorating psoriasiform pathologic change of guinea pigs. There was no significant difference in scores of positive group, high-dose and low-dose groups of chlorogenic acid. For chlorogenic acid, score of low-dose group was superior to that of high-dose group, and its dose-effect relationship was not dose-dependent. Under light microscope, each drug administration group presented alleviation of hyperkeratosis and parakeratosis phenomenon, increase of stratum granulosum, thinning of spinous layer, and reduction of inflammatory cell infiltration degree, suggesting chlorogenic acid can treat psoriasis.

2) Effects on Hepatic and Renal Function

One-factor analysis of variance indicated that compared with other groups, urea nitrogen, serum creatinine, glutamate pyruvate transaminase (ALT), and glutamic-oxalacetic transaminase (AST) of positive control group were obviously higher, as shown in Table 1. That suggested chlorogenic acid had protective effect on hepatic and renal function, with good safety.

TABLE 1

Effect of chlorogenic acid on hepatic and renal function of guinea pigs

| Index | High dose (n = 11) | Low dose (n = 11) | Positive group (n = 11) | Blank group (n = 10) | Model (n = 11) |
| --- | --- | --- | --- | --- | --- |
| AST (u/L) | 24.80 ± 2.57 | 29.10 ± 7.29 | 110.80 ± 6.75* | 33.00 ± 4.99 | 41.00 ± 3.49 |
| ALT (u/L) | 32.30 ± 6.07 | 33.40 ± 7.26 | 98.40 ± 4.14* | 39.30 ± 5.89 | 35.80 ± 4.29 |
| Urea nitrogen (mmol/) | 4.98 ± 0.71 | 4.92 ± 0.63 | 10.67 ± 0.33* | 5.32 ± 0.90 | 6.02 ± 0.98 |
| Serum creatinine (μmol/L) | 87.27 ± 4.67 | 88.33 ± 7.80 | 175.43 ± 3.67* | 88.71 ± 3.57 | 90.81 ± 2.27 |

Note:
Compared with blank group, *P < 0.05.

Example 2 Pharmacodynamic Test of Chlorogenic Acid According the Present Invention for Treatment of Psoriasis (Psoriasis Pustulosa)

Experimental Study:
1. Materials
1) Animals

Kunmin mice, with weight of 18-22 g, are provided by Experimental Animal Center of Sichuan University. Animal grade: first class; license number: No. 10.

2) Drug

Chlorogenic acid is provided by Sichuan Jiuzhang Biochemical Science and Technology Development, Co. Ltd, with a batch number: 130601.

2. Experimental Method
1) Grouping of Animals

Kunmin mice were randomly divided into 3 groups. Blank control group: according to body weight, about 0.5 ml of peanut oil was administrated to mice by gavage everyday; for high-dose group of chlorogenic acid (20 mg·kg$^{-1}$), chlorogenic acid was administrated to each mouse at a dose of 0.4 ml/20 g by peritoneal injection; for low-dose group of chlorogenic acid (10 mg·kg$^{-1}$), chlorogenic acid was administrated to each mouse at a dose of 0.4 ml/20 g by peritoneal injection. Following phasic points were observed, i.e. before administration (day 0), days 1, 2, 4, 6 after administration.

2) Experimental Method

After a piece of sterile gelatin sponge (1 cm$^2$) was immersed in 0.75% zymosan A for 30 min, it was placed in peritoneal cavity of mice by surgery, and mice received standard diet. 24 hours after surgery, 5 mice of same phasic point were decapitated, and the gelatin sponges were taken out and stored in 0.5 ml cell eluant for culturing 30 min at 37° C., respectively. The gelatin sponges were washed with 0.01 mol/LPBS0.5 ml thrice, respectively, and the eluant was collected, passed through 40 μm nylon screen cloth, centrifuged, and the volume was 0.5 ml. Cells in above eluants were counted by automatic blood cell counter, and the amount of polymorphonuclear leukocytes (PMN) was read.

3. Results

For different dose groups of chlorogenic acid, comparison of PMN transport numbers at different phasic points was shown in Table 2. In different dose groups of chlorogenic acid, transport numbers of PMN were significantly different (P<0.01), and in a group, transport numbers of PMN at each time point were also significantly different (P<0.01).

TABLE 2

Comparison of PMN transport numbers at different phasic points in different dose groups of chlorogenic acid (×10$^9$/L)

| Groups | Day 0 | Day 1 | Day 2 | Day 4 | Day 6 |
| --- | --- | --- | --- | --- | --- |
| Blank control group | 7.30 ± 1.57 | 9.10 ± 1.29 | 7.10 ± 1.75 | 7.45 ± 2.99 | 7.38 ± 1.49 |
| High dose group | 7.60 ± 6.07 | 1.54 ± 0.26 | 1.20 ± 2.14 | 1.15 ± 0.89 | 1.10 ± 1.29 |
| Low dose group | 6.98 ± 1.71 | 4.92 ± 2.63 | 2.67 ± 1.33 | 1.98 ± 0.90 | 1.62 ± 0.58 |

4. Conclusion

PMN plays an important role in development of psoriasis pustulosa. Regression of pustules in patients with psoriasis pustulosa was accompanied by notable decrease of PMN chemotactic activity, and if drugs can inhibit the normal chemotactic activity of PMN, it is shown that drugs can have therapeutic effects on psoriasis pustulosa by inhibiting chemotactic activity of PMN.

Above experimental results indicate that chlorogenic acid can significantly reduce chemotactic activity of PMN in mice, and compared with low dose group of chlorogenic acid, high dose group has a stronger inhibitory action on chemotactic activity of PMN in mice. Chlorogenic acid can inhibit expression of adhesion molecules on the surface of PMN, thus it has good effects on the treatment of psoriasis pustulosa.

The invention claimed is:

1. A method for treating psoriasis, comprising:
   applying a medicament to a patient having psoriasis, wherein the medicament comprises an effective amount of chlorogenic acid.
2. The method according to claim 1, wherein the medicament is effective in treating psoriasisvulgaris and psoriasis pustulosa.
3. The method according to claim 1, wherein the medicament is a pharmaceutical preparation comprising the effective amount of chlorogenic acid and a pharmaceutically acceptable adjuvant or auxiliary ingredient.
4. The method according to claim 3, wherein the pharmaceutical preparation contains 1-3000 mg chlorogenic acid per preparation unit.
5. The method according to claim 4, wherein in said pharmaceutical preparation, a concentration of chlorogenic acid used is 10-40 mg/kg.
6. The method according to claim 3, wherein said medicament is an oral preparation, an external preparations, or an injection.

* * * * *